US00PP30036P2

(12) United States Plant Patent
Ammerlaan

(10) Patent No.: US PP30,036 P2
(45) Date of Patent: Dec. 25, 2018

(54) ***GASTERALOE* PLANT NAMED 'OVROCKS01'**

(50) Latin Name: ***Gasteraloe* Guillaumin**
Varietal Denomination: OVROCKS01

(71) Applicant: Johannes Hendrikus Adrianus Ammerlaan, Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/731,924

(22) Filed: Aug. 24, 2017

(30) Foreign Application Priority Data

Jul. 18, 2017 (QZ) ..... PBR 2017/1816

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Anne Marie Grunberg
(74) *Attorney, Agent, or Firm* — Samuel R. McCoy, Jr.

(57) ABSTRACT

A new and distinct cultivar of *Gasteraloe* plant named 'OVROCKS01' which is characterized by a compact plant size with a flattened globular profile, an abundance of short, broad, and relatively thin succulent foliage which is spirally arranged in a basal rosette, dark green foliage which is densely covered with orbicular papillae, as well as the stability of these characteristics from generation to generation.

4 Drawing Sheets

Latin name of the genus and species: The Latin name of the genus and species of the novel variety disclosed herein is *Gasteraloe* Guillaumin.

Variety denomination: The inventive variety of *Gasteraloe* disclosed herein has been given the variety denomination 'OVROCKS01'.

CROSS REFERENCE TO RELATED APPLICATIONS

This application claims priority to the Community Plant Variety Rights application number 2017/1816, filed on Jul. 18, 2017, which is herein incorporated by reference.

BACKGROUND OF THE INVENTION

Parentage: 'OVROCKS01' originated as a naturally occurring, whole-plant mutation of an unnamed *Gasteraloe* plant (not patented). In May of 2013 the inventor discovered the mutation at a commercial greenhouse in Bleiswijk, the Netherlands, growing amongst a crop of the parent plant. The mutation was noted for its compact habit and spirally arranged foliage and was subsequently isolated for further evaluation in order to confirm the distinctness and stability of the characteristics first observed. Upon confirmation of distinctness and stability, 'OVROCKS01' was selected for commercialization.

Asexual Reproduction: Asexual reproduction of the new cultivar 'OVROCKS01', by way of rooting leaf cuttings, was first initiated in May of 2013 at the inventor's commercial greenhouse in Bleiswijk, the Netherlands. The claimed plant has since been asexually propagated by way of meristematic tissue culture propagation. Through four subsequent generations, the unique features of this cultivar have proven to be stable and true to type.

SUMMARY OF THE INVENTION

The cultivar 'OVROCKS01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS01'. These characteristics in combination distinguish 'OVROCKS01' as a new and distinct *Gasteraloe* cultivar:

1. 'OVROCKS01' exhibits an abundance of relatively thin succulent foliage, spirally arranged in a basal rosette; and
2. 'OVROCKS01' exhibits a compact size with a flattened globular profile; and
3. 'OVROCKS01' exhibits short and broad, ovate foliage with finely dentate leaf margins and an apiculate apex with a soft mucronate tip; and
4. 'OVROCKS01' exhibits mature foliage with a relaxed attitude, that is slightly curved downward, with juvenile foliage in the innermost whorls appearing to be more upright; and
5. 'OVROCKS01' exhibits dark green foliage which is densely covered with orbicular papillae which bear short, soft spines towards the apex.

BOTANICAL DESCRIPTION OF THE PLANT

Figure 1:
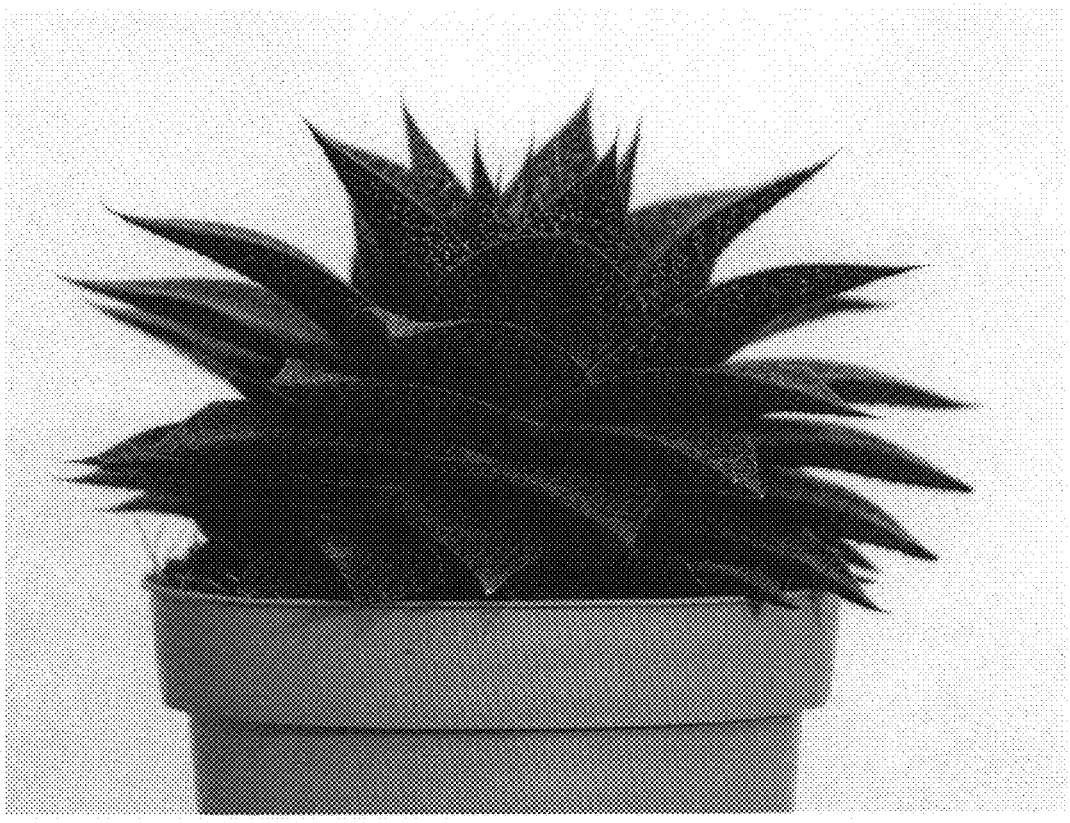
FIG. 1 illustrates, as nearly true as it is reasonably possible to make the same in color photographs of this type, an exemplary plant of 'OVROCKS01' grown in a commercial greenhouse in Bleiswijk, the Netherlands. This plant is approximately 16 months old, shown planted in a 10.5 cm container.
Figure 2:
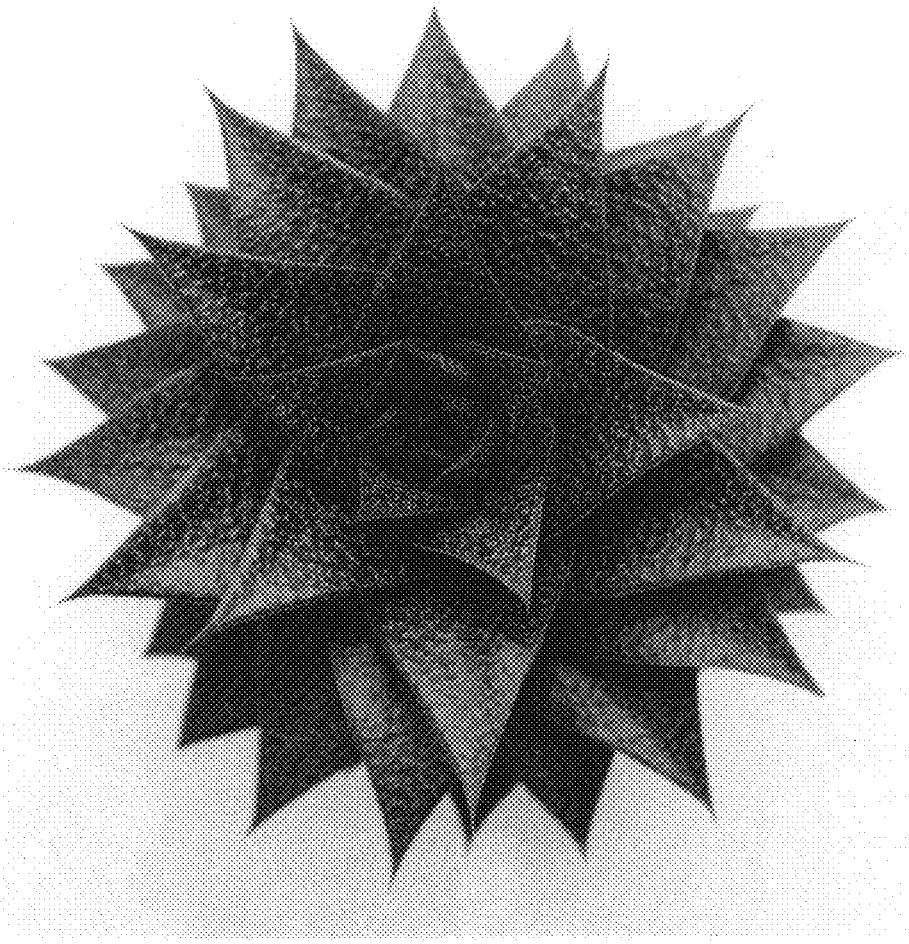
FIG. 2 illustrates, as nearly true as it is reasonably possible to make the same in color photographs of this type, the typical foliage arrangement of 'OVROCKS01'.
Figure 3:
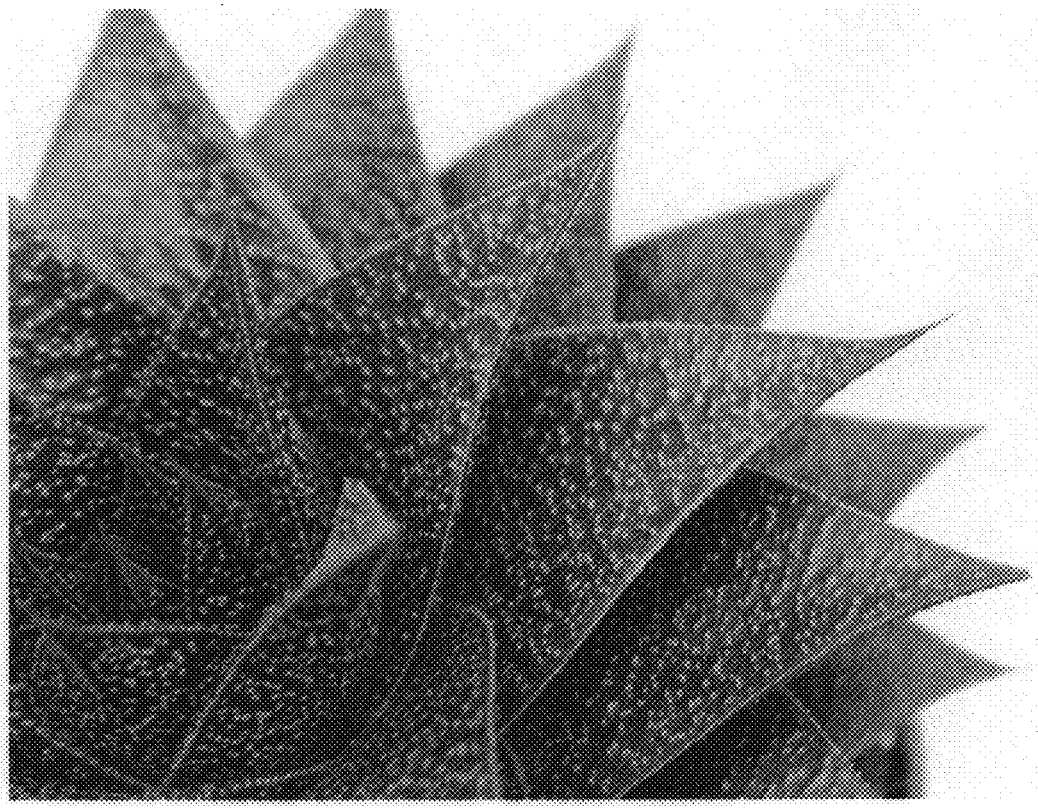
FIG. 3 illustrates, as nearly true as it is reasonably possible to make the same in color photographs of this type, the adaxial surface of the mature foliage 'OVROCKS01'.
Figure 4:
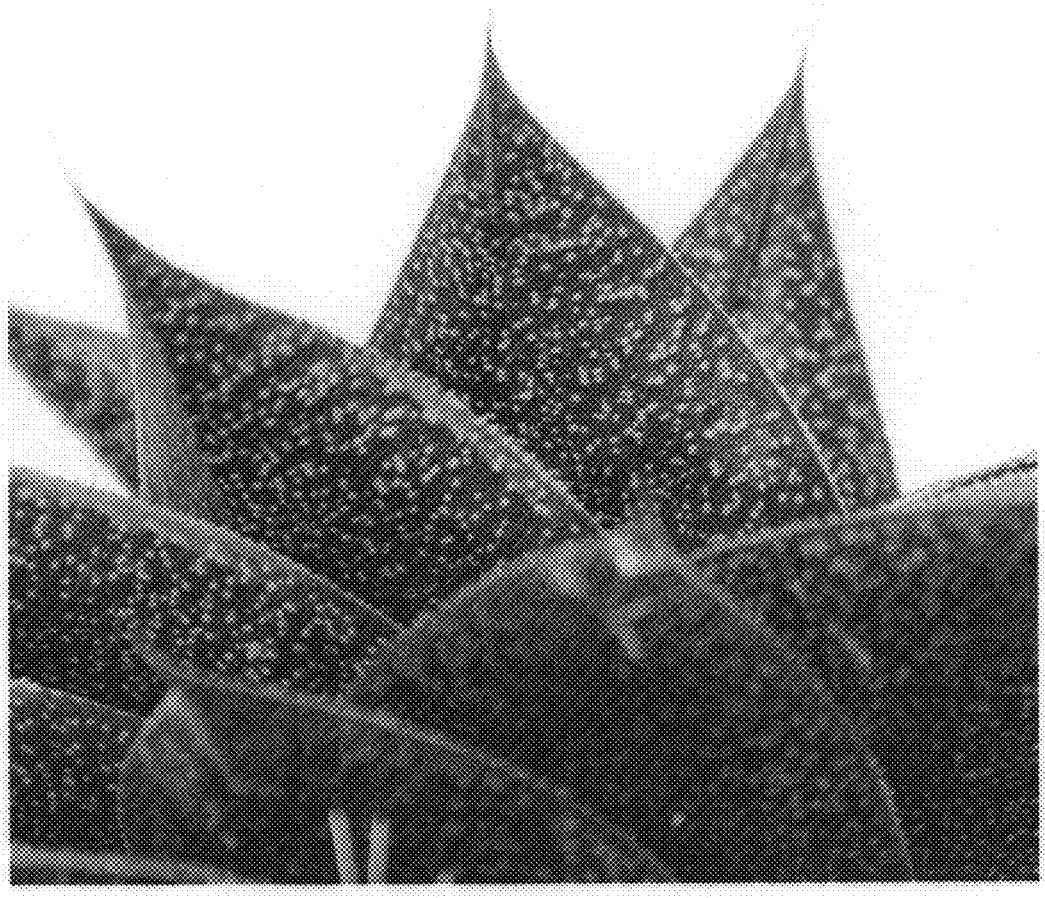
FIG. 4 illustrates, as nearly true as it is reasonably possible to make the same in color photographs of this type, the abaxial surface of the mature foliage 'OVROCKS01'.

The following observations and measurements made in June of 2017 describe averages from a sample set of six specimens of 16 months old 'OVROCKS01' plants grown in 10.5 cm nursery containers at commercial greenhouse in Bleiswijk, the Netherlands. Plants were produced using conventional greenhouse production protocols for *Gasteraloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS01' and a comparison with the parent and closest known comparator is provided below.

Plant description:

*Growth habit*.—Succulent perennial with foliage growing in a non-branched basal rosette.

*Plant form*.—Flattened globular; compact.

*Height from soil level to top of foliar plane*.—9.0 cm.

*Plant spread*.—Average of 16.4 cm.

*Growth rate*.—Moderate.

*Plant vigor*.—Moderate.

*Propagation*.—Type — Leaf cuttings. Time to initiate rooting — Approximately 90 days at 21 degrees Celsius. Crop time — Approximately 16 months to produce a marketable plant in a 10.5 cm container.

*Disease and pest resistance or susceptibility*.—Neither resistance nor susceptibility to typical *Gasteraloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally placed in a rosette.

*Division*.—Simple.

*Attachment*.—Sessile.

*Quantity*.—Approximately 65 leaves per rosette.

*Shape*.—Ovate succulent leaves.

*Dimensions*.—7.8 cm long, 4.1 cm wide, and 0.7 cm thick, on average.

*Aspect*.—Slightly concave.

*Attitude*.—Slightly curved downward.

*Apex*.—Apiculate with a soft mucronate tip.

*Base*.—Broad cuneate.

*Margin*.—Finely dentate; teeth have an average length of 0.03 cm and are colored green, nearest to RHS 143B. Margins are not undulated or lobed.

*Texture, adaxial surface*.—Glabrous and densely covered with papillae, presenting as orbicular dots, each approximately 0.5 mm high and 0.5 mm; papilla bearing short, soft spines towards the apex; average length of the spines is 0.3 mm, at maturity.

*Texture, abaxial surface*.—Glabrous and densely covered with papillae, presenting as orbicular dots, each approximately 0.5 mm high and 0.5 mm in diameter; papilla bearing short, soft spines towards the apex; average length of the spines is 0.3 mm, at maturity.

*Luster, adaxial surface*.—Moderately glossy.

*Luster, abaxial surface*.—Glossy.

*Color*.—Juvenile foliage, adaxial surface — Green, nearest to RHS 139A but darker, and fading to yellow-green towards the base, nearest to RHS 146A; leaf densely covered with papillae which are colored yellow-green, nearest to RHS 147D with a green-white center, nearest to RHS 157D. Juvenile foliage, abaxial surface — Nearest to in between green, RHS 139A, and yellow-green, RHS 147D, but darker; fading to yellow-green towards the base, nearest to in between RHS 146C and 146D; leaf densely covered with papillae which are colored yellow-green, nearest to RHS 148D with a green-white center, nearest to RHS 157D. Mature foliage, adaxial surface — Nearest to in between green, RHS 139A, and greyed-green, RHS N189A, but much darker; fading to yellow-green, nearest to RHS 144A, and ultimately to white, nearest to RHS N155C, towards the base; leaf densely covered with papillae which are colored yellow-green, nearest to RHS 147B. Mature foliage, abaxial surface — Nearest to in between green, RHS 139A, and yellow-green, RHS 147A, but darker; fading to green, nearest to RHS 143B, and ultimately to white, nearest to RHS N155C, towards the base; leaf densely covered with papillae which are colored yellow-green, nearest to RHS 147B. Venation — No venation is visible.

*Petiole*.—No petiole; leaves are sessile.

Inflorescence: No flowering has been observed to date.

COMPARISONS WITH THE PARENT PLANT

Plants of the new cultivar 'OVROCKS01' differ from the parent, an unnamed *Gasteraloe* plant (not patented), in the following characteristics described in Table 1 below.

TABLE 1

| Characteristic | 'OVROCKS01' | The parent. |
|---|---|---|
| Plant height. | More compact than the parent. | Taller than 'OVROCKS01'. |
| Abundance of foliage. | More leaves in the rosette. | Fewer leaves in the rosette. |
| Foliage; occurrence of spines on the papillae. | Fewer spines along the margins towards the apex. | More spines along the margins towards the apex. |

COMPARISONS WITH THE CLOSEST KNOWN COMPARATOR

Plants of the new cultivar 'OVROCKS01' differ from the commercial variety, *Gasteria* 'VVT04' (not patented in the United States; European Union CPVO grant EU33165) in the following characteristics described in Table 2 below.

TABLE 2

| Characteristic | 'OVROCKS01' | 'WT04' |
|---|---|---|
| Abundance of foliage. | More leaves in the rosette. | Fewer leaves in the rosette. |
| Foliage arrangement. | Foliage has a more relaxed attitude. | Not spirally arranged. |
| Foliage attitude. | | Foliage is more upright. |
| Length of foliage. | Shorter than 'WT04'. | Longer than 'OVROCKS01'. |
| Width of foliage. | Wider at the base. | Narrower at the base. |
| Thickness of foliage. | Thinner than 'WT04' | Thicker than 'OVROCKS01'. |
| Foliage; prominence of spines on the papillae. | Less prominent. | More prominent. |

That which is claimed is:

1. A new and distinct variety of *Gasteraloe* plant named 'OVROCKS01', substantially as described and illustrated herein.

* * * * *